United States Patent [19]
Sponholtz

[11] Patent Number: 5,670,118
[45] Date of Patent: Sep. 23, 1997

[54] COLOR CODED TEST WELLS

[75] Inventor: Dennis Keith Sponholtz, Chantilly, Va.

[73] Assignee: Dynex Technologies, Inc., Sullyfield Circle Chantilly, Va.

[21] Appl. No.: 687,019

[22] Filed: Jul. 25, 1996

[51] Int. Cl.$^6$ ...................................... C12M 1/20
[52] U.S. Cl. .............. 422/102; 422/119; 435/288.4; 435/305.2
[58] Field of Search .................. 422/102, 119, 422/99; 435/288.4, 305.2

[56] References Cited

U.S. PATENT DOCUMENTS

| | | |
|---|---|---|
| 4,319,841 | 3/1982 | Suovaniemi et al. |
| 4,431,307 | 2/1984 | Suovaniemi. |
| 4,510,119 | 4/1985 | Hevey .................... 422/71 |
| 4,891,321 | 1/1990 | Hubscher ............ 422/102 X |
| 5,152,965 | 10/1992 | Fisk et al. .............. 422/102 |
| 5,254,314 | 10/1993 | Yu et al. ................ 422/102 |
| 5,308,584 | 5/1994 | Vauramo. |
| 5,470,536 | 11/1995 | Jarvimaki. |

*Primary Examiner*—Jeffrey Snay
*Attorney, Agent, or Firm*—Donald C. Casey, Esq.

[57] ABSTRACT

A method and procedure for color coding cuvettes used in laboratory tests without contaminating the interior thereof or changing its binding properties is described. In the procedure of this invention, transparent plastic cuvettes are utilized which are flat bottomed and have a depending rim surrounding the flat bottom. The depending surface of the rim then has color applied thereto by a conventional technique either hot stamping, or by ultra-violet cured silk screen printing. In either event, a colored surface is formed on the rim. The transparent walls of the cuvette then by light pipe effect give the appearance that the color surrounds the upper opening of such cuvette when in fact the opening is of transparent plastic.

10 Claims, 2 Drawing Sheets

COLOR CODED TEST WELLS

FIELD OF THE INVENTION

This invention relates to laboratory testing apparatus and in particular to a coded test apparatus for ready identification of test samples wherein cuvettes are used, and in which trays of color coded, transparent plastic cuvettes are provided for reliable and reproducible test results.

DESCRIPTION OF THE PRIOR ART

Immunoassays have been used for many years for a wide variety of biological tests. Such assays, in wide use in testing laboratories, often use immobilized enzymes as such or in combination with other methods. Typically, these tests are carried out in plastic cuvettes and the results are determined by reading the reagent reaction with a photometer wherein exciting light is directed into each cell and the results read, or a luminometer is used wherein a chemical reaction generates a light signal within the cell which is read. Other techniques are also well known.

Common to such testing procedures, however, is the use of individual cuvettes to contain individual samples. Trays of cuvettes have been marketed for many years under the trademark MICROTITER. Such trays contain 96 cuvettes in a matrix of 8 rows of 12 columns molded as a plastic tray. The cuvettes in each tray are visually identified by the raised letters A-H designating 8 rows across, and the raised numbers 1-12 identifying the 12 columns. Other types of machine readably identifiers are known. MICROTITER trays are of manufactured by DYNEX Technologies, Inc., formerly Dynatech Laboratories, Inc. of Chantilly, Va.

In many laboratory situations, however, MICROTITER trays contain too many cuvettes and it is desired to provide less than 96 test wells. On the other hand, many testing or reading machines are adapted to receive a tray of dimensions similar to the MICROTITER tray. Accordingly, frames containing one or more individual columns or strips of eight cuvettes are available and trays in which individual cuvettes may be mounted as well as strips thereof are known. For example, such break-apart strips of cuvettes are marketed by the afore mentioned company under its trademark DIVIDASTRIPS and the frame matrix is marketed under its trademark REMOVAWELL. Other examples of such cuvette matrix arrays are described for example, in U.S. Pat. Nos. 4,319,841, 4,431,307, 5,308,584 and 5,470,536, among others.

In situations where a small number of tests dictates the use of only one or less than 12 strips of 8 cuvettes it is highly desirable to be able to identify visually the strips of cuvettes which contain the samples tested according to a particular test protocol. For example, the tests may be conducted on body fluid from one or more individuals or different tests may be conducted on such different body fluids, but in any event, it is necessary to be able to distinguish and identify the individual test wells. While the frame which retains the strips of wells normally will have the letters identifying rows and numbers identifying columns these identifiers would typically be of the same plastic material as the frame itself, and therefore, difficult to distinguish visually. Furthermore, if the strips of wells are identical, unless they are retained in specifically identified rows in a frame throughout the entire procedure, they would be indistinguishable. In other words, outside of the frame having raised identification letters and numbers each strip of wells is indistinguishable from another.

In the case of strips of wells molded from transparent plastic material it is known to color code such strips by imprinting a color on the upwardly opening edge of each cuvette. The same color would be used on all cuvettes in a single strip. One procedure for color coding in this fashion is a method known as "hot stamping" wherein aluminum foil with an ink on a surface thereof overlies the strips of wells and a heated platen is applied to the upper aluminum foil surface. The heat causes the ink to fuse with the well surface, and when the aluminum strip is removed a ring of color surrounds the opening. This procedure has a disadvantage in that the ink can flake from the aluminum foil during application and fall into the test well. In addition, hot stamping is a slow process.

An alternative process is to print on the opening surface of each well using a silk screen method. In this situation the ink solvent can enter the test well and introduce impurities. More importantly, however, many inks are ultra-violet cured and therefore the inked surface must be exposed to a flash of ultra-violet light for curing. When the ultra-violet light flash enters the interior of the cell through the opening it can effect the binding properties of the cell wall, so that identical properties are not-exhibited by what would appear to be identically constructed wells. The ultra-violet flash can cause a change in the affinity of the plastic for accepting, for example, enzymes and this change in the affinity then, effecting the binding properties of the cell, can affect the reproducability of individual tests based thereon.

For many years individual plastic wells have been marketed with an optical window in the base thereof. Whether such a window was present or not, it was discovered that when the base of each cuvette is flat and is intended to transmit light therethrough, the transmission properties are affected by scratching or abrasion of the outer bottom surface. In order to protect the outer surfaces of such flat bottom cuvettes, rims were developed which extend downwardly from the base of each cuvette to thereby protect the base from scratching. This procedure is used typically in cuvettes constructed of transparent plastic material whether the base is used as an optical window or not. Clearly, if the cuvette strip is constructed of pigmented plastic protection of the bottom thereof from scratching would not be important as the presence of the pigment is intended to block the transmission of light therethrough, in any event.

SUMMARY OF THE INVENTION

It has been discovered, however, that in the case of clear plastic molded strips of cuvettes, the individual strips can be color coded without affecting the binding properties of the interior cuvette walls by the application of color to the lower surface of the rim which surrounds the base of each individual cuvette. The color then when the cuvettes are viewed from above appears to be on the upper surface even though it is on the base because the walls of each cuvette transmit the color as a light pipe. When such cuvettes are viewed either from directly above or from the side and above they appear as if the wells have a colored ring surrounding the upper opening when in fact the color is on the base thereof.

Color may be applied to the base by any conventional technique. In the case of silk screen printing, it has further been discovered that ultra-violet light flash techniques used for curing the ink do not effect the binding properties of the cell as the ultra-violet flash does not penetrate the base of the individual cuvettes.

Accordingly it is an object of this invention to provide a method for color coding plastic cuvettes without effecting the test properties of the individual cuvettes.

It is another object of this invention to provide a method for color coding strips of micro-cuvettes wherein the cuvettes are molded from transparent plastic with a rim surrounding a flat bottom and color is applied to the lower surface of the rim.

It is a further object of this invention to provide a color coded test well in transparent plastic wherein the wells are formulated in break apart strips and individual wells are separable from the strips, but are molded from clear plastic having a flat base and the rim surrounding the base, wherein the color coding is a color material applied to the surface of the rim only.

It is a further object of this invention to provide a method for identifying individual strips of clear plastic cuvette test wells wherein each well has a flat bottom and a depending rim surrounding the bottom and wherein each strip is color coded by the application of color to the lower surface of each rim either by hot stamping or by silk screen printing.

These and other objects will become readily apparent with reference to the drawings and following description herein.

DETAILED DESCRIPTION OF THE INVENTION

Figure 1:
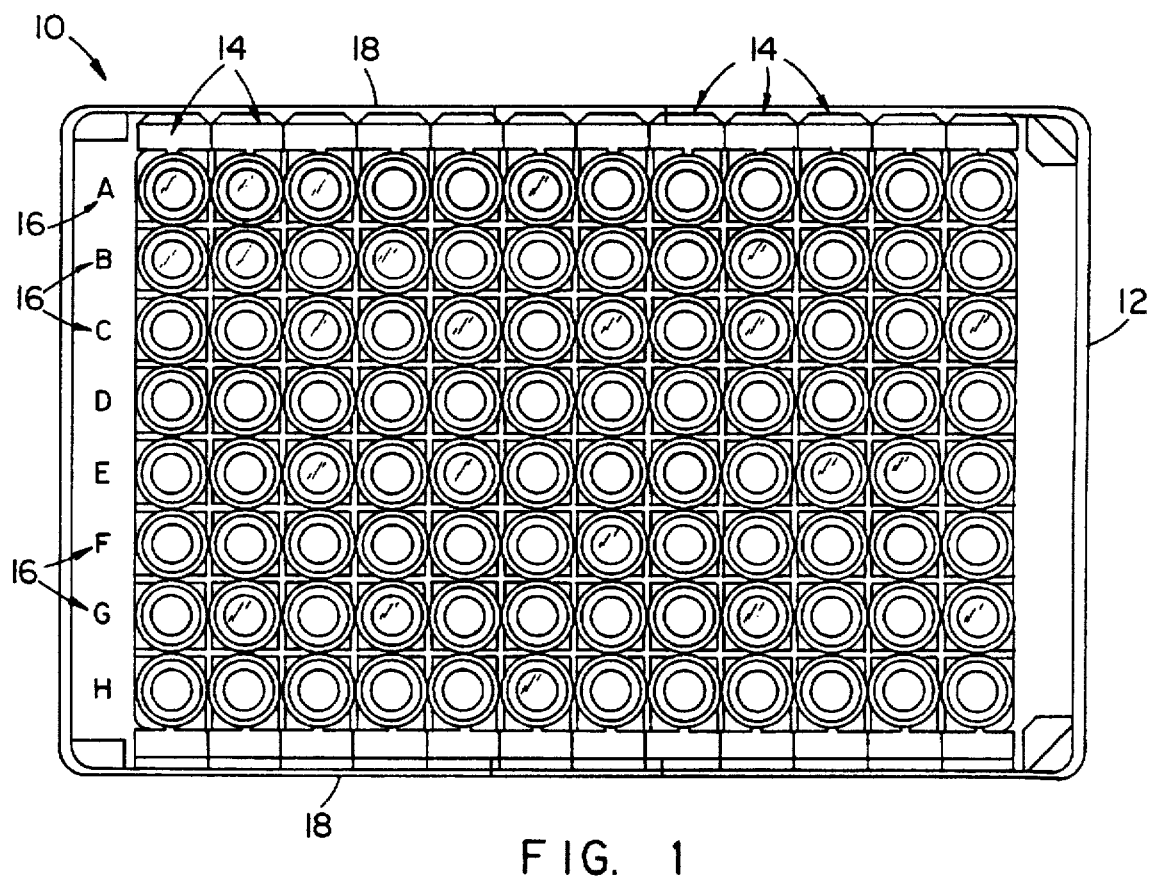
FIG. 1 is a top view of an array of individual strips of cuvettes disposed in a frame.

With attention to the drawings and to FIG. 1 in particular, a typical tray of cuvettes 10 incorporates a frame member 12 which forms a matrix for receiving individual strips 14 of break apart cuvettes. A side of the frame 12 exhibits raised letters 16 forming A-H which letters identify rows of cuvettes. These letters are integral with the plastic material forming the frame 12. With attention to FIG. 2, each strip 14 of cuvettes 20 typically contains 8 cuvettes and is a unitary plastic molding having handles or lips 22 at either end thereof. The strips then are placed in the matrix frame 12 so that the handles or lips 22 rest upon the frame sides 18. The frame 12 then will be dimensioned to contain 12 of such strips 14 disposed side-by-side forming 12 columns. Typically, the side 18 of the frame 12 will have a number 1-12 raised and disposed to identify each of the 12 columns. The number would be obscured by the overlying lip 22 as shown in FIG. 1.

Figure 2:
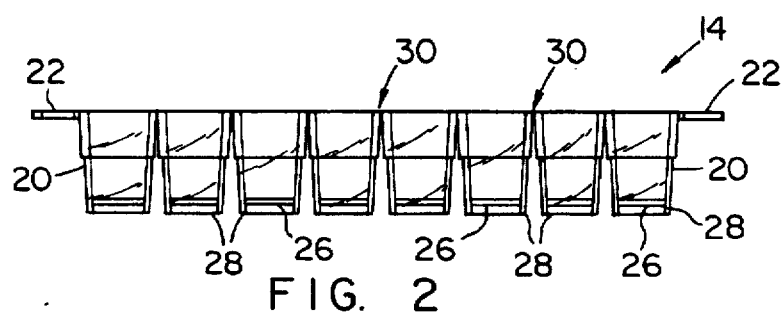
FIG. 2 is a side view of a strip of 8 such cuvettes.
Figure 3:
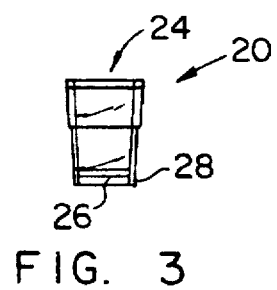
FIG. 3 is a side view of an individual cuvette from said strip.

With reference further to FIGS. 2 and 3, each individual cuvette 20 is a cup shaped member 24, opening upwardly and a base 26. Surrounding the base 26 is a depending flange 28 which is intended to protect the base 26 from scratches and abrasion.

Accordingly, when cuvette strips 14 are molded of transparent plastic and are disposed in frame 12, the letters A-H will be visible from above as being integral with the base frame 12, and numbers 1-12 (not shown) would be visible through the lips 22 of each strip along side 18. Because these letters and numbers, however, are molded in the plastic forming the frame 12 they would be of the same color, and therefor would be not readily visually distinguishable.

Each strip 14 of cuvettes as shown herein can be manufactured from any conventional plastic such a polystyrene. However, this invention is intended to be limited to transparent strips. While a single strip 14 of cuvettes is shown herein it will be obvious to those skilled in the art that multiple strips may be joined and that this invention is not intended to be limited to a specific single strip of cuvettes. Furthermore, each cuvette 20 and each strip 14 is a joined by a breakable plastic bridge 30 which can be broken so that an individual cuvette 20 can be used for a test if desired.

Figure 4:
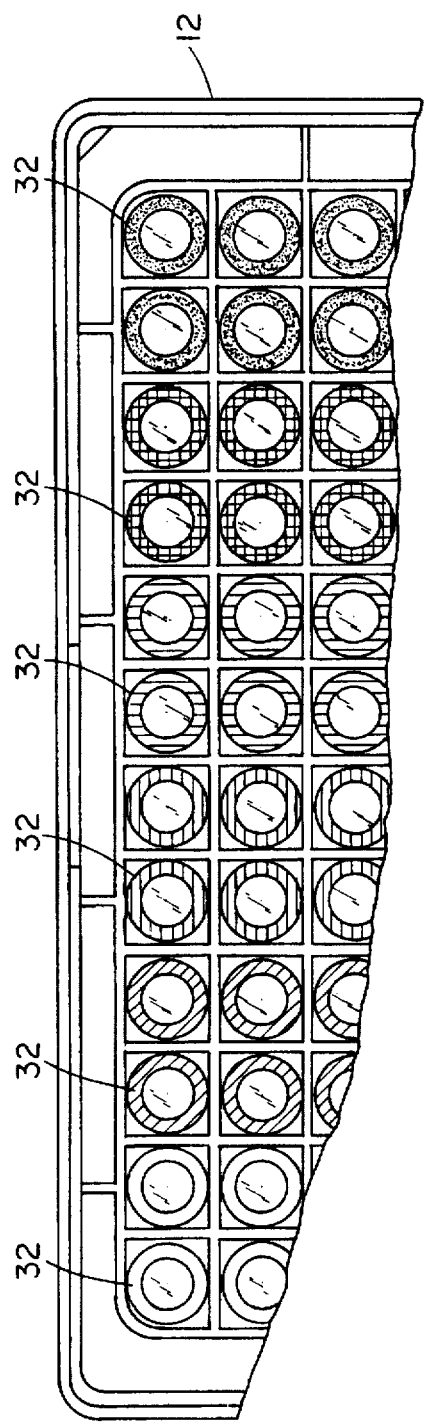
FIG. 4 is a fragmentary bottom view of the cuvette array of FIG. 1.
Figure 5:
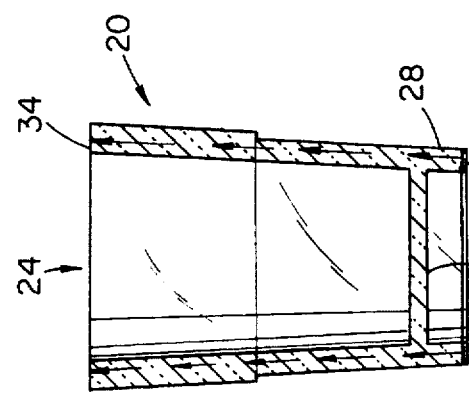
FIG. 5 is a cross-sectional view of an individual cuvette of this invention illustrating the light pipe effect through the walls thereof.

With attention to FIGS. 4 and 5, this invention, intended to be used with transparent cuvettes 20 having a depending rim 28 surrounding the flat base 26 is intended to have color applied to form a color surface 32 at the bottom of rim 28. When viewed from above, the light traveling upwardly through the sides of cuvette 20 as shown in FIG. 5, will be exhibited as a color surrounding the opening 24 at the top thereof. In other words, when viewed from above, with transparent cuvettes 24, the upper surface 34 will appear to be colored whereas the colored surface is actually surface 32 at the base. In the fragmentary view of FIG. 4, there is shown a bottom view wherein the bottom surfaces of rows of cuvettes which are retained in frame 12 have different colors applied thereto. As will be obvious to those skilled in the art, while technically feasible, individual cuvette bottom surfaces 32 in a strip 14 could be individually colored, but economically, the strips 14 typically would be of the same color and if multiple strips are integrally molded (not shown) normally all of the bottom rims of the individual cuvettes therein would have the same color. As in the case of individual cuvettes, however, technologically, it would be possible to color individual strips in a multiple strip column if economically feasible.

The colored surface 32 typically may be applied by "hot stamping" as is well known in the art. This procedure while slow, can be utilized without the likelihood of contaminating the interior of the individual cuvette 20 A colored ink on an aluminum sheet or aluminum foil is overlaid over the rims 28 and a heated platen (not shown) is applied to the outer surface of the aluminum strip of foil sufficiently to transfer the ink to the heat softened plastic rim 28 to form surface 32.

In a preferred technique, silk screen printing is used onto the rim 28 to form the surface 32 and the printed surface is cured typically with an ultra-violet light flash. As noted above, it has been determined that the interior of individual cuvette 20 is not affected by the exterior application of ultra-violet light to cure the surface 32.

Alternatively any conventional technique for forming surface 32 will be contemplated within the scope of this invention.

In summary, it has been determined that the risk of contaminating the interior of individual cuvettes by the application of color thereto can be avoided by applying the color to the base thereof. More specifically in the case of transparent cuvettes formed with flat bottoms and a rim surrounding the bottom, the color is applied to the depending rim and it has been discovered that when viewed from above or from above and to the side, the light pipe affect of the cuvette walls will give the illusion that opening is surrounded by a color ring rather than by the transparent plastic cuvette walls. While the invention is limited to transparent plastic cuvettes, the cuvettes can be in the form of one or more strips or individuals, or multiple integral strips which are typically retained in a matrix frame or individual cuvettes can be maintained in such a frame.

In this way, utilizing the color coded cuvettes of this invention, laboratory tests can be preformed utilizing less than 96 of such cuvettes down to a single cuvette and the cuvettes utilized can be color coded to identify, for example, different tests of different body fluids or the fluids of different individuals tested.

It will be readily seen by one of ordinary skill in the art that the present invention fulfills all of the objects set forth above. After reading the foregoing specification, one of ordinary skill will be able to effect various changes, substitutions or equivalents and various other aspects of the invention as broadly disclosed herein. It is therefore granted hereon the protection granted hereon be limited only by the definition contained in the appended claims and equivalents thereof.

I claim:

1. In a transparent plastic cuvette for use in biological testing, consisting of a cylindrical upwardly opening cup having a flat bottom, said flat bottom being surrounded by a depending flange of said plastic material, the improvement comprising:

a colored surface formed on the depending flange only, said colored surface being visually observable through said upper opening to identify said cuvette from above whereby light passing upwardly from said bottom will appear to color the upper opening thereof.

2. The cuvette of claim 1 wherein said surface includes ultra-violet cured ink.

3. Color coded plastic cuvettes comprising a plurality of interconnected transparent plastic cuvettes, each cuvette being an upwardly opening cylinder having a flat bottom and a protective depending flange surrounding the outer surface of said bottom, said cuvettes having a surface of said flange only coated a predetermined color, said colored surface being visually observable through said upper opening so that when viewed from above said cuvettes will appear to have colored upper openings.

4. The cuvettes of claim 3 wherein said cuvettes are integrally connected adjacent the upper openings and from a least one elongated strip.

5. The cuvettes of claim 4 wherein each strip comprises a column of eight cuvettes.

6. A method for identifying test cuvettes wherein said cuvettes are transparent, upwardly opening plastic cylinders each having a flat bottom and a flange depending therefrom to surround said bottom comprising: selecting an identifying color and integrally applying said color to the bottom surface of said flange only to form a colored flange surface, said colored surface being visually observable through said upper opening.

7. The method of claim 6 wherein a plurality of said cuvettes are interconnected to form at least one column and cuvettes in each column have the same predetermined color applied.

8. The method of claim 7 wherein eight cuvettes are interconnected adjacent the upper opening thereof to form a column.

9. The method of claim 6 wherein said color is applied by hot stamping.

10. The method of claim 6 wherein said color is applied by silk screen printing using ultra-violet cured ink.

* * * * *